United States Patent
Johnstone

(10) Patent No.: US 8,568,421 B2
(45) Date of Patent: Oct. 29, 2013

(54) APPARATUS AND METHOD FOR ALIGNING AND POSITIONING IMPLANTS IN A BODY

(75) Inventor: Alan John Johnstone, Aberdeen (GB)

(73) Assignee: Grampian Health Board, Aberdeen (GB)

( * ) Notice: Subject to any disclaimer, the term of this patent is extended or adjusted under 35 U.S.C. 154(b) by 1686 days.

(21) Appl. No.: 10/512,759

(22) PCT Filed: Apr. 28, 2003

(86) PCT No.: PCT/GB03/01794
§ 371 (c)(1),
(2), (4) Date: Oct. 26, 2004

(87) PCT Pub. No.: WO03/092515
PCT Pub. Date: Nov. 13, 2003

(65) Prior Publication Data
US 2005/0177175 A1    Aug. 11, 2005

(30) Foreign Application Priority Data
Apr. 27, 2002 (GB) .................................. 0209719.4

(51) Int. Cl.
*A61B 17/60* (2006.01)
*A61F 2/00* (2006.01)

(52) U.S. Cl.
USPC .......................................................... 606/97

(58) Field of Classification Search
USPC ............. 606/86 R, 87, 96–98, 912; 623/1.34; 604/103.1, 362, 529
See application file for complete search history.

(56) References Cited

U.S. PATENT DOCUMENTS

| | | | |
|---|---|---|---|
| 4,803,976 A | 2/1989 | Jenny et al. | |
| 4,865,025 A | 9/1989 | Buzzi et al. | |
| 4,976,713 A | 12/1990 | Landanger et al. | |
| 6,027,506 A | 2/2000 | Faccioli et al. | |
| 6,036,696 A * | 3/2000 | Lambrecht et al. | 606/97 |
| 6,520,969 B2 | 2/2003 | Lambrecht et al. | |
| 6,656,189 B1 * | 12/2003 | Wilson et al. | 606/97 |
| 7,083,624 B2 * | 8/2006 | Irving | 606/87 |

* cited by examiner

*Primary Examiner* — Anu Ramana
(74) *Attorney, Agent, or Firm* — Drinker, Biddle & Reath, LLP

(57) ABSTRACT

Apparatus for handling of at least one implant for a body is provided. The apparatus has a radio translucent portion and a radio-opaque marking. The apparatus can optionally comprise a jig affixable to an intramedullary nail, which can be used to determine the position of holes to be drilled through a bone which align with holes in the nail. The radio-opaque marking will appear on an x-ray and can be used to indicate the relative alignment of the jig and the nail.

42 Claims, 13 Drawing Sheets

APPARATUS AND METHOD FOR ALIGNING AND POSITIONING IMPLANTS IN A BODY

This Application is the U.S. National Phase Application of PCT International Application No PCT/GB03/01794 filed Apr. 28, 2003.

FIELD OF THE INVENTION

The present invention relates to an apparatus and method for aligning and positioning implants in a body, and is particularly useful for the positioning and securing of intra-medullary bone fixings such as nails.

DESCRIPTION OF THE RELATED ART

It is common practice to support fractures in long bones by intra-medullary nails. The nail is inserted into the medullary canal of the long bone, and is held in place by screws that are driven laterally through the bone at each end of the nail. The screws also pass through pre-drilled holes in the end of the intra-medullary nail, thereby reducing or preventing movement of the nail while the fracture is healing. Holes must be bored laterally through the bone in order to insert the screws, and these must be aligned with the pre-drilled holes in the ends of the intra-medullary nail. In order to position and drill the holes accurately in the bone, a jig is commonly employed.

The jig is attached to the protruding (proximal) end of the nail after insertion of the nail into the medullary canal, and typically extends generally parallel to the nail. The jig has pre-drilled holes that align with the holes in nail when the jig and the nail are properly attached and aligned. This works quite satisfactorily for the proximal holes to be drilled through the bone, but since the jig is only attached to the nail at one end, and the jig and nail can be quite long (up to around 60 cm), it can be very difficult to align the distal holes in the jig with the distal holes in the nail.

SUMMARY OF THE INVENTION

According to the present invention there is provided apparatus for handling of an implant for a body, the apparatus having a radio-translucent portion and a radio-opaque marking.

The apparatus typically comprises a jig for positioning of implants such as fixings for bone nails, plates or other structural support devices inserted into a body.

The radio-translucent portion can be formed of plastics material, but in preferred embodiments the jig is generally made from rigid materials, so materials such as carbon fibre are preferred. The radio-opaque marking can be one or more strips of metal (or other radio-opaque materials such as lead paint) applied to the carbon fibre, or incorporated therein. The radio-opaque markings are typically in the form of parallel lines. The markings can preferably be provided on the jig itself, but in some embodiments, the markings can be provided on a separate alignment device or guide that can be connected to the jig, or placed in a defined position relative to it.

The jig typically has markings or guide holes to indicate positions on the bone to drill holes to receive fixing screws or other implants such as pins or wires. In preferred embodiments, the jig can receive drill sleeves to be placed against the bone so that holes can be drilled through the drill sleeves into the bone at a position on the bone that is aligned with the holes in the nail, or which hit a target in the bone e.g. the head of femur.

The jig may have an alignment adjustment mechanism to adjust the alignment of the jig relative to the patient, and consequently relative to the nail inserted into the medullary canal of the bone in the limb, or other target on the patient. The alignment adjustment mechanism can typically comprise a screw-threaded device such as a screw-threaded shaft that can adjust the alignment of the nail and the jig in small increments. The shaft can engage within a screw thread on the jig, or a nut, and can terminate in a pad.

The jig can typically have a hinge to allow movement of an arm of the jig having markings or guide holes to indicate the position of the holes to be drilled through the bone. The hinge can be in the form of a true hinge, or in the form of a semi-flexible joint having a degree of resilience.

In preferred embodiments for use with intra-medullary nails, the jig may be attached to the nail. In some of these embodiments the jig can be deliberately misaligned with the nail at an initial position, so that the alignment of the jig and the nail must be adjusted by the adjustment mechanism before the correct alignment is achieved. In preferred embodiments, the distal end of the jig is inclined towards the nail, and/or out of the plane of the nail. Typically the jig is attached at only one end (e.g. the protruding end) of the nail, so that the lateral end of the jig can be moved into the correct alignment with the nail by the adjustment mechanism. This gives the advantage that the final aligned position of the jig relative to the nail is only reached after forcing the jig into that aligned position, against the resilience of the jig, which seeks to return the jig to the misaligned initial position. Therefore, the final aligned position is less prone to variation as a result of the opposing forces acting on the jig.

Typically the jig is attached to one end of an intra-medullary bone fixing such as a nail, and the assembly is viewed through an x-ray image intensifier so that the radio-opaque markings on the jig can be superimposed upon the image of the bone fixing, which is typically also radio-opaque. The alignment between the distal end of the jig and the nail located in the medullary canal can then be checked and adjusted by slight movements of the jig relative to the limb of the patient, before the holes are drilled through the bone to insert the fixing screws through the nail.

In a simple embodiment of the invention, the jig comprises a flat member that extends in a single plane that is generally parallel to the nail that is inserted into the medullary canal of the fractured bone. However, in certain more complex embodiments, the jig can be formed in more than one plane. For example, the jig can be generally L-shaped or arcuate (e.g. semi-cylindrical) instead of planar, and can extend circumferentially over different parts of the limb. Non-planar embodiments can typically extend around 90-180° (or more, eg up to 360°) of the limb, so that lateral holes can be drilled through the bone at various angles, allowing antero-posterior, medio-lateral and diagonal fixings to be inserted through the bone to connect with corresponding holes in the nail, or with other targets in the patient.

The implant to be handled is preferably a fixing for an intra-medullary nail, but other implants of a permanent or of a more transitory nature can also be handled with the apparatus, such as drill bits, guide wires for drills, screws such as bone screws, k-wires, blade plates and pins such as external fixator pins etc. Certain embodiments of the invention are particularly suitable for correct placing of implants that are not visible on X-rays. The apparatus is also very useful for image guided surgical procedures, where, for example, a hole must be drilled along a very precise path into e.g. a spinal vertebra, for injection of e.g. hydroxyappatite paste into the bone, and is particularly useful for surgical procedures where there is very little margin for error. Using the apparatus, the path of the drill can be visualised e.g. by X-rays before the hole is drilled, thereby increasing the accuracy of the drilling, and reducing the risks to the patient.

The invention also provides a method of aligning a jig with a body implant, the method comprising providing a radio-translucent portion of the jig with radio-opaque markings, and assessing alignment of the jig and the body implant by observing the alignment of the body implant relative to the radio-opaque markings.

The jig can be hand-held or can be adapted to be attached to the body, either to the surface of the body or to a portion of the skeleton. In some embodiments the jig can be attached to wires or pins braced against the surface of the bone, or to a frame attached to such wires or pins.

DETAILED DESCRIPTION OF THE INVENTION

Figure 1:
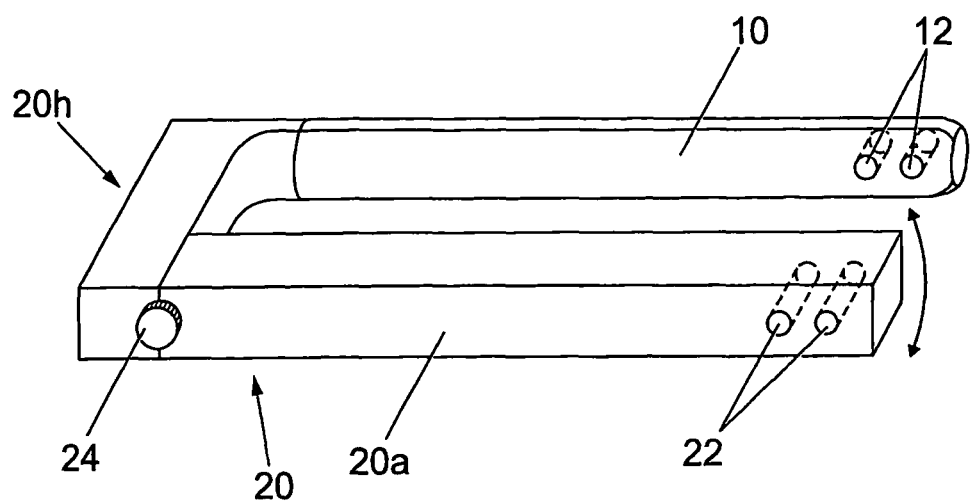
FIG. 1 shows a schematic perspective view of a first jig.

Referring now to FIG. 1, an intra-medullary nail 10 adapted to be inserted into the medullary canal of a long bone has a proximal end attached to a jig 20, and a distal end with holes 12 to receive fixing screws (not shown). The jig 20 has a head portion 20h adapted to attach releasably to the proximal end of the nail 10 by means of a bolt (not shown) driven through the head 20h and into an axial socket on the nail 10. The jig 20 also has an arm 20a that is attached to the head 20h by a hinge having a ratchet 24 allowing the angle of the arm 20a to be varied relative to the nail 10. The hinge can optionally incorporate a locking mechanism to lock the arm 20a at a predetermined attitude relative to the nail 10, and this arrangement can usefully replace the ratchet mechanism 24.

The arm 20a of the jig has a pair of holes 22 in the distal end (there could be any number of holes provided). The distal holes 22 in the arm 20a align with the distal holes 12 in the nail 10 when the arm 20a is aligned with the nail 10. The holes 22 are each adapted to receive a drill sleeve through which a drill bit can be inserted in order to drill a hole through the bone in alignment with the holes 12 in the nail 10.

The arm 20a is formed from carbon fibre, but another material that is radio-translucent could alternatively be used. The arm 20a has metal wires 26 embedded within it, or attached to one of its lateral surfaces. The wires 26 are generally disposed in a parallel array along the length of the arm 20a, although it should be noted that other patterns of markers can optionally be used, and parallel arrays are not essential. Since the metal wires are radio-opaque, they are distinguishable when the assembly of the jig and nail are viewed in a x-ray image intensifier, or other x-ray detection device.

As an alternative to axial metal wires, planar metal strips (not shown) could be embedded within the arm 20a parallel to the axis of the arm. The metal strips could be aligned in horizontal planes vertically spaced from each other in the arm. Such strips would appear as narrow lines if the nearest face of arm 20a is oriented exactly perpendicular to the beam from the image intensifier. However, if the arm 20a is misaligned, the strips would appear as thicker rectangles. Thus, such metal strips provide the advantage of allowing judgement of the rotational alignment of the arm, and hence also of the nail, as well as the axial alignment of the nail.

The planar metal strips could also be arranged in the plane of the axis of the arm and in another plane perpendicular thereto, so that the two sets of lines interconnect with one another. In this embodiment the grid of strips can indicate alignment in more than one plane by presenting a minimal cross-section to the viewer, and can indicate misalignment by increased cross-section of the observed grid.

Figures 4, 5:
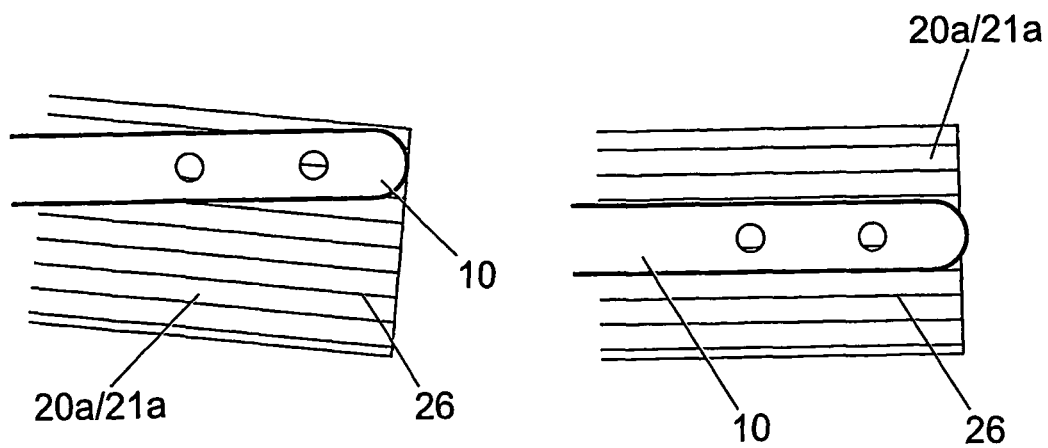
FIG. 4 shows the jig misaligned with the nail.
FIG. 5 shows the jig and nail properly aligned.

In use, the intra-medullary nail 10 is inserted into the medullary canal of the patient's limb and the jig 20 attached to its proximal end. Initially, the arm 20a is placed out of alignment with the nail 10, and the view through the image intensifier is similar to that shown in FIG. 4, where the nail 10 is seen superimposed upon the parallel array of wires 26, and the misalignment between the nail 10 and the jig arm 20a is apparent. The arm 20a is then pivoted around the hinge relative to the nail 10 until the parallel array of wires 26 is aligned with the nail 10 in the image intensifier, as shown in FIG. 5. When the arm 20a is in the position shown in FIG. 5, with the parallel array of wires 26 being aligned with the nail 10, the operator can be sure that the holes 22 in the jig are aligned perfectly with the holes 12 in the nail 10. It should be noted that the markings on the arm need only be brought into alignment with a part of the nail, or with other markings on the nail, and that the whole of the nail does not need to be aligned with the markings on the jig, in order to verify its correct position.

When the holes 22 are perfectly aligned with holes 12, the ratchet 24 is adjusted to fix the angle of the arm 20a relative to the nail 10. Typically, guide wires (K-wires) are now inserted through holes 22 and holes 12 and are secured in the cortical bone on the opposite side of the bone to the jig 20. A cannulated drill is then inserted over the guide wires to drill holes through the bone. The holes preferably extend as far as the cortical bone on the far side of the bone from the jig 20. The drill is then removed and cannulated screws are inserted over the guide wires and screwed into the bone to secure the nail 10 to the bone. Jig 20 is then detached from the nail 10, and the nail 10 is typically left in the bone until the fracture has healed.

The above-described method is a preferred method of operation; however, modifications may be made. It is not necessary to use the guide wires, as the holes 22, 12 could simply be used to align the drill correctly. In this case, the screws would not need to be cannulated.

Figure 2:
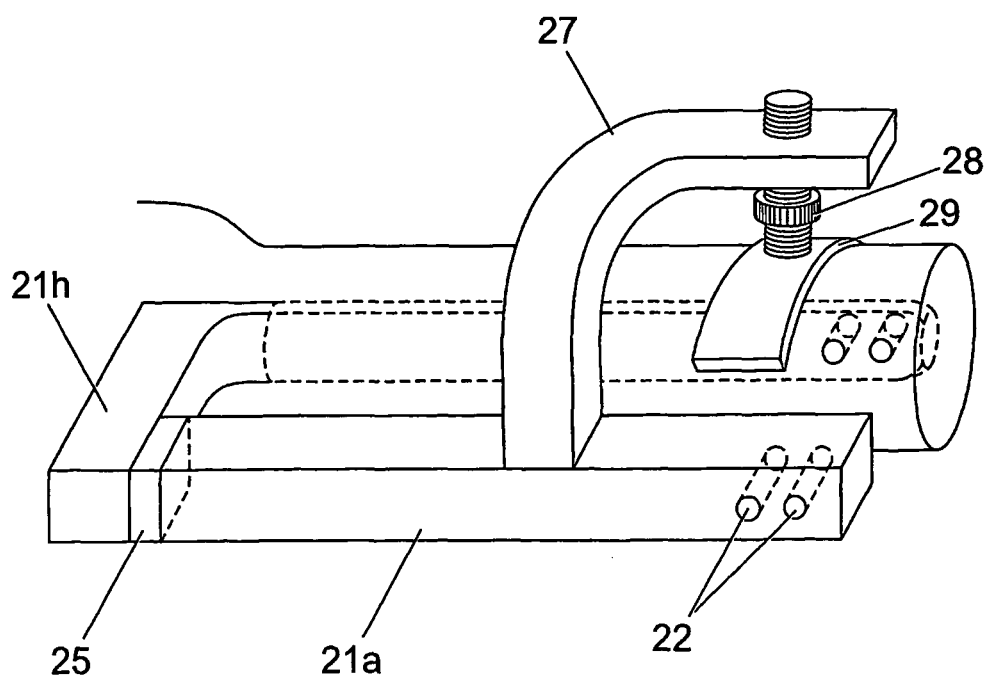
FIG. 2 shows a similar view of a second jig.
Figure 3:
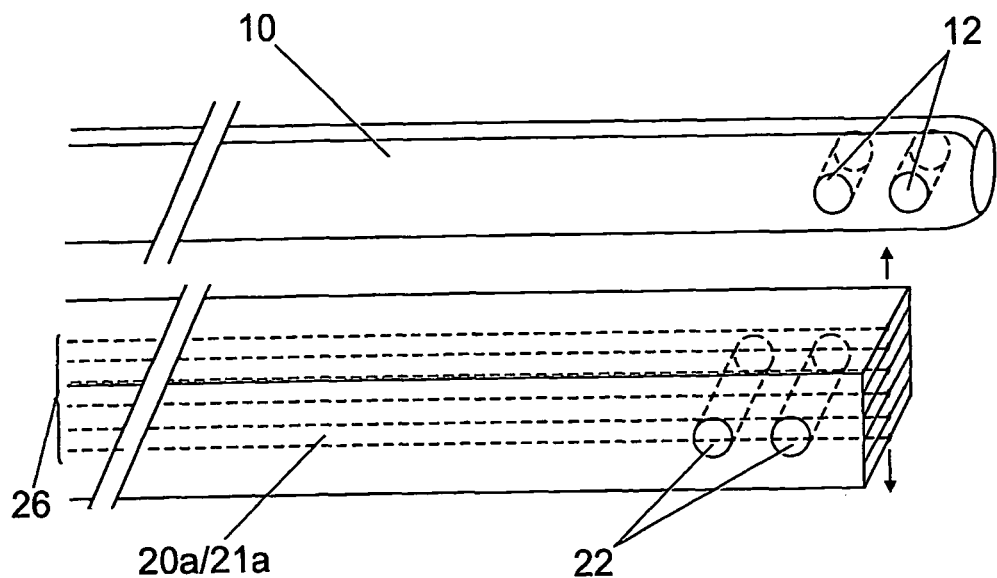
FIG. 3 shows a close up view of the FIG. 1 and FIG. 2 jig.

FIG. 2 shows an alternative embodiment of a jig 21 in which the arm 21a is attached to the head 21h by means of a semi-flexible joint 25. The arm 21a is again formed from carbon fibre, and has metallic wires 26 similar to the first embodiment shown in FIG. 1. The FIG. 2 embodiment also has a stabiliser arm 27 with a threaded shaft passing through a plain aperture in the arm 27, and terminating in a padded foot 29. The arm 21a is biased out of alignment with the nail 10 so that the two initially adopt relative positions similar to those shown in FIG. 4. In use, the foot 29 is placed on top of the patient's limb and a nut 28 adjusted to push the limb of the patient down relative to the arm 21a. Since the nail 10 is embedded within the medullary canal of the long bone in the patient's limb, this has the effect of bringing the arm 21a and the nail 10 into alignment. The nut 28 is driven up the shaft until the arm 21a and the nail 10 are pulled into the position shown in FIG. 5, where the metal wires 26 can be seen to be in alignment with the nail 10. At this point, in a similar manner to the FIG. 1 embodiment, the alignment of the nail 10 and the arm 21 can be verified, and the drill sleeves can be inserted through the holes 22, and holes drilled through the bone with confidence that they are aligned with the holes 12 in the distal end of the nail 10.

The method steps described above with reference to FIG. 1 concerning insertion of guide wires, drilling holes in the bone with a cannulated drill inserted over the guide wires and inserting screws to secure the nail 10 to the bone are all equally applicable here.

This embodiment has additional advantages over the FIG. 1 design, in that the contact between the stabiliser arm 27 and the limb helps to maintain the alignment, and reduces the likelihood of force exerted by the weight of the drill, or force misapplied by the operator, moving the arm 21a out of alignment with the nail 10 during the drilling procedure. In addition, the deliberate bias of the arm 21a out of alignment with the nail 10 forces the operator to observe the alignment of the nail 10 and the arm 21a until the two are properly aligned with one another. Furthermore, since the arm 21a is subject to opposing forces exerted by the stabiliser arm 27 on the one hand and the natural bias of the semi-flexible joint 25 on the other, it is less likely to deviate from its position once alignment has been established.

Figure 6:
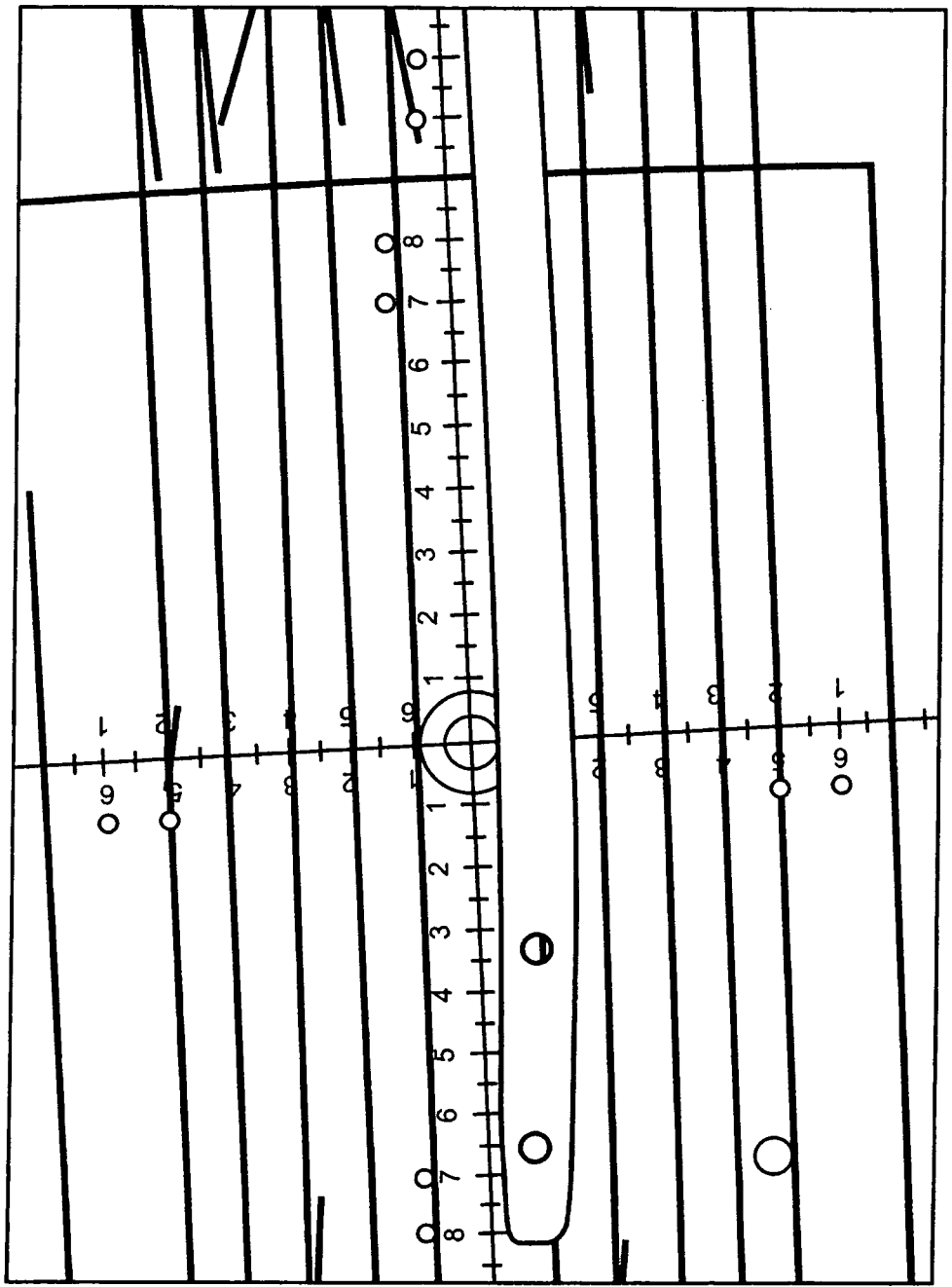
FIG. 6 is a radiograph of a nail aligned with a jig.
Figure 7:
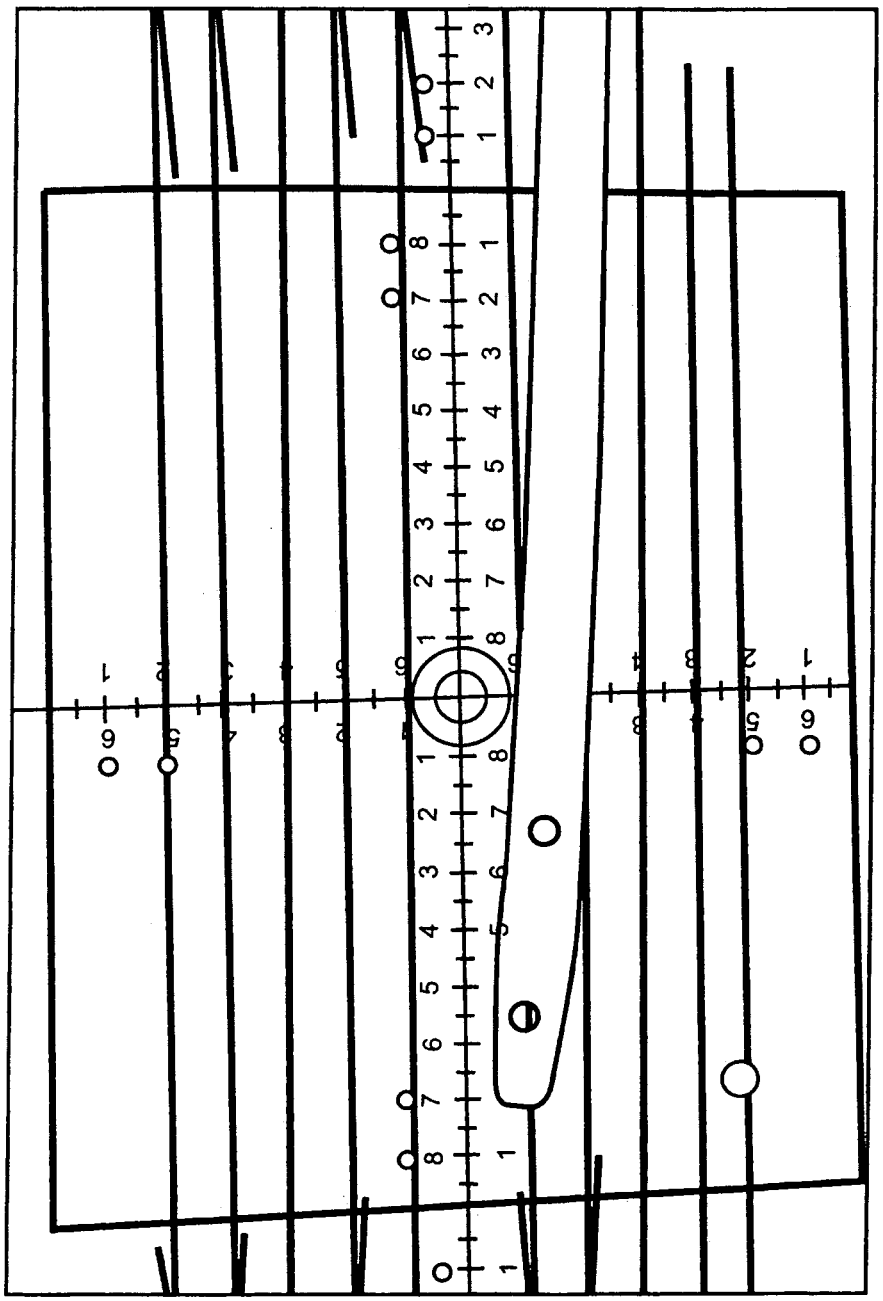
FIG. 7 is a radiograph of a nail misaligned with a jig.
Figure 8:
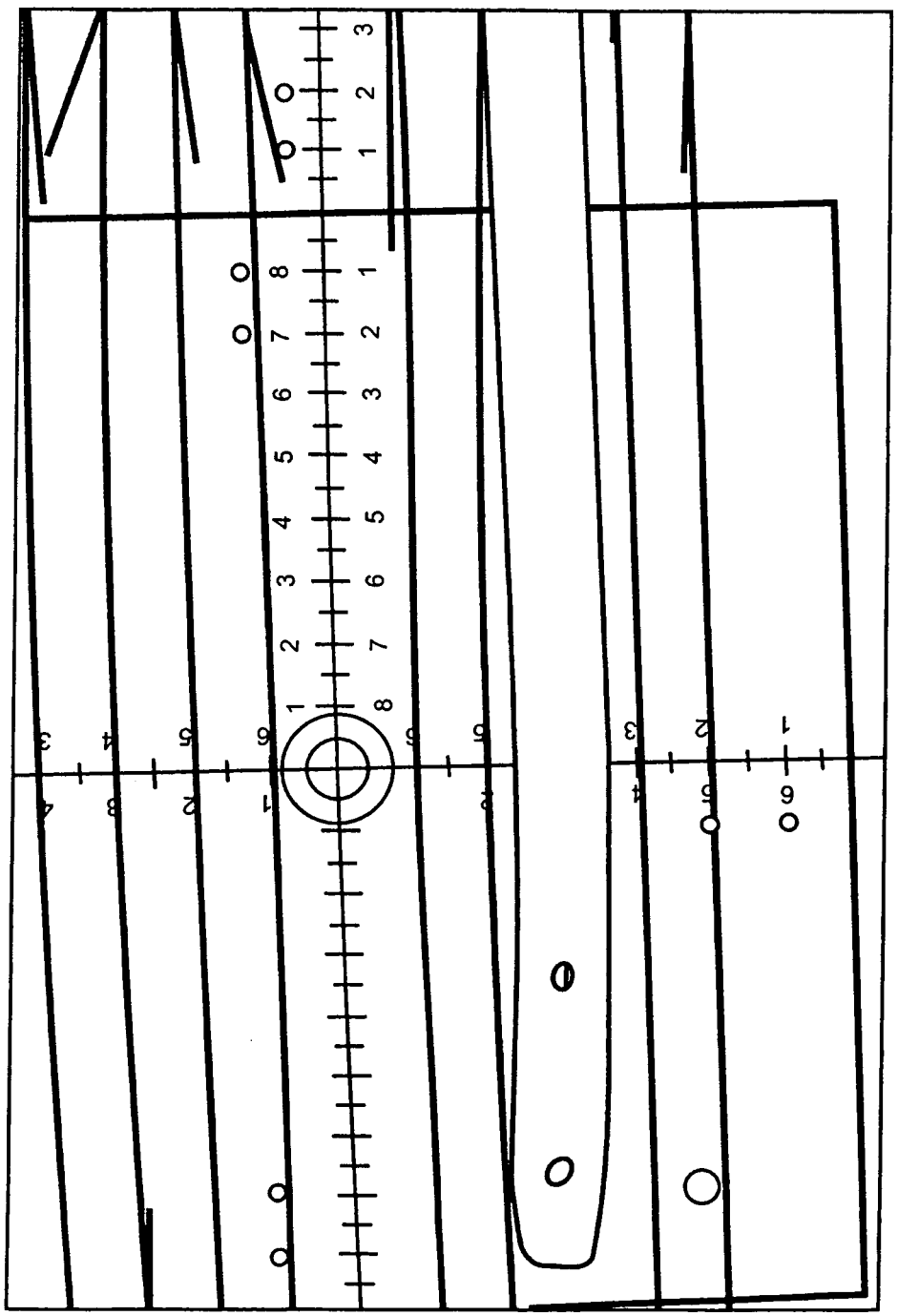
FIG. 8 is a view similar to FIG. 6 with the camera displaced 20° down.
Figure 9:
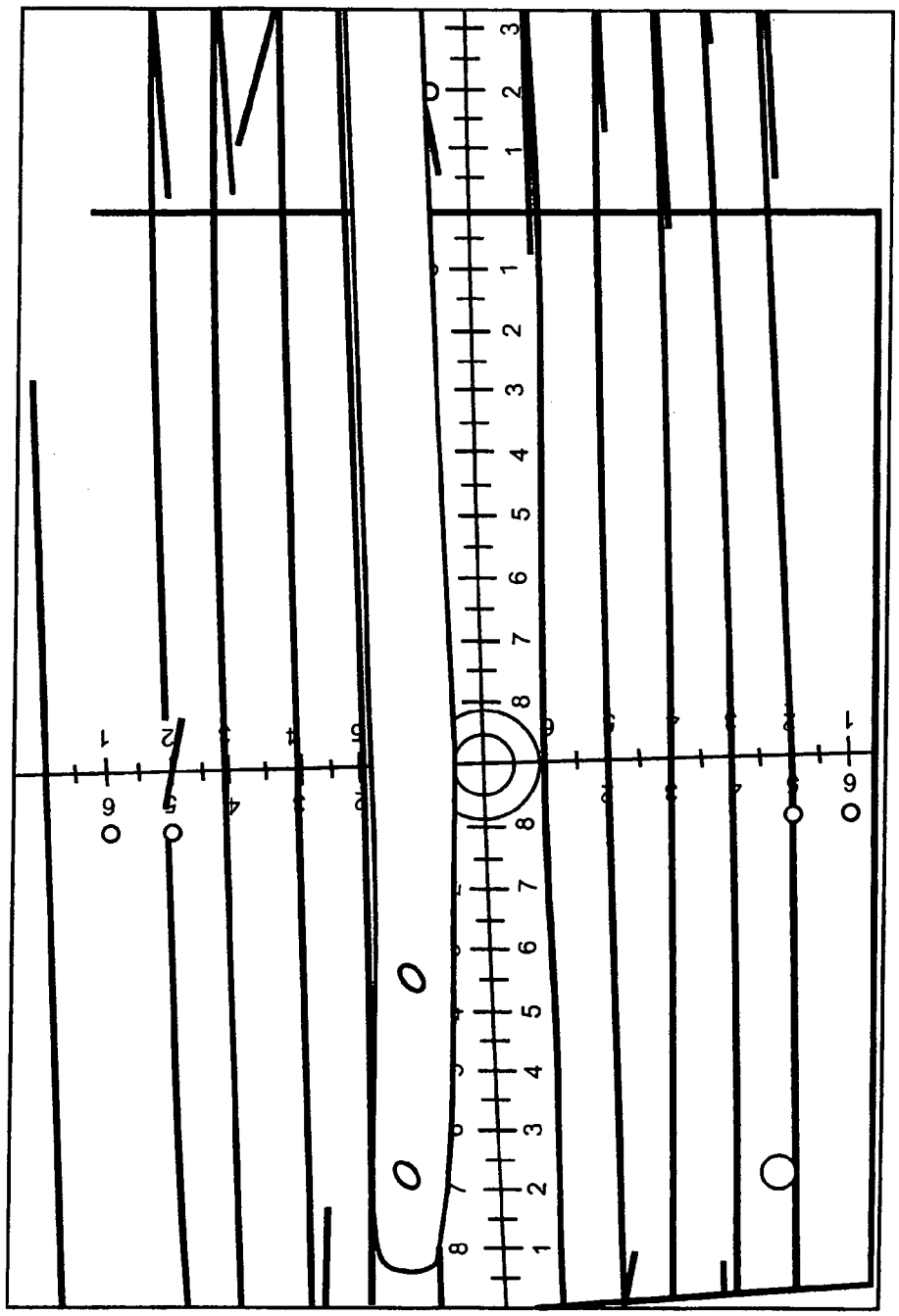
FIG. 9 is a view similar to FIG. 6 with the camera displaced 15° up.
Figure 10:
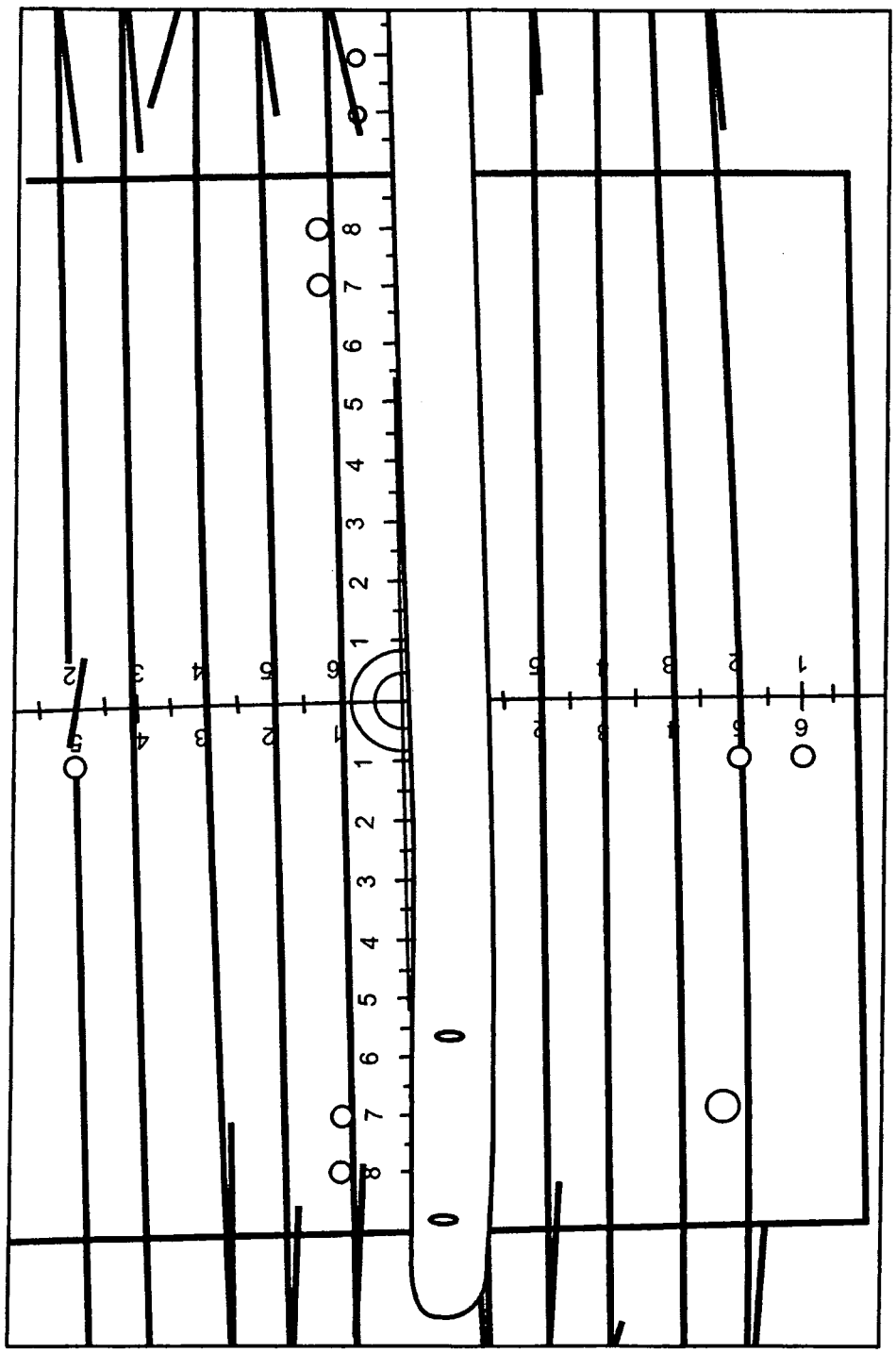
FIG. 10 is a view similar to FIG. 6, with the camera horizontal but displaced 15° craniocaudally.
Figure 11:
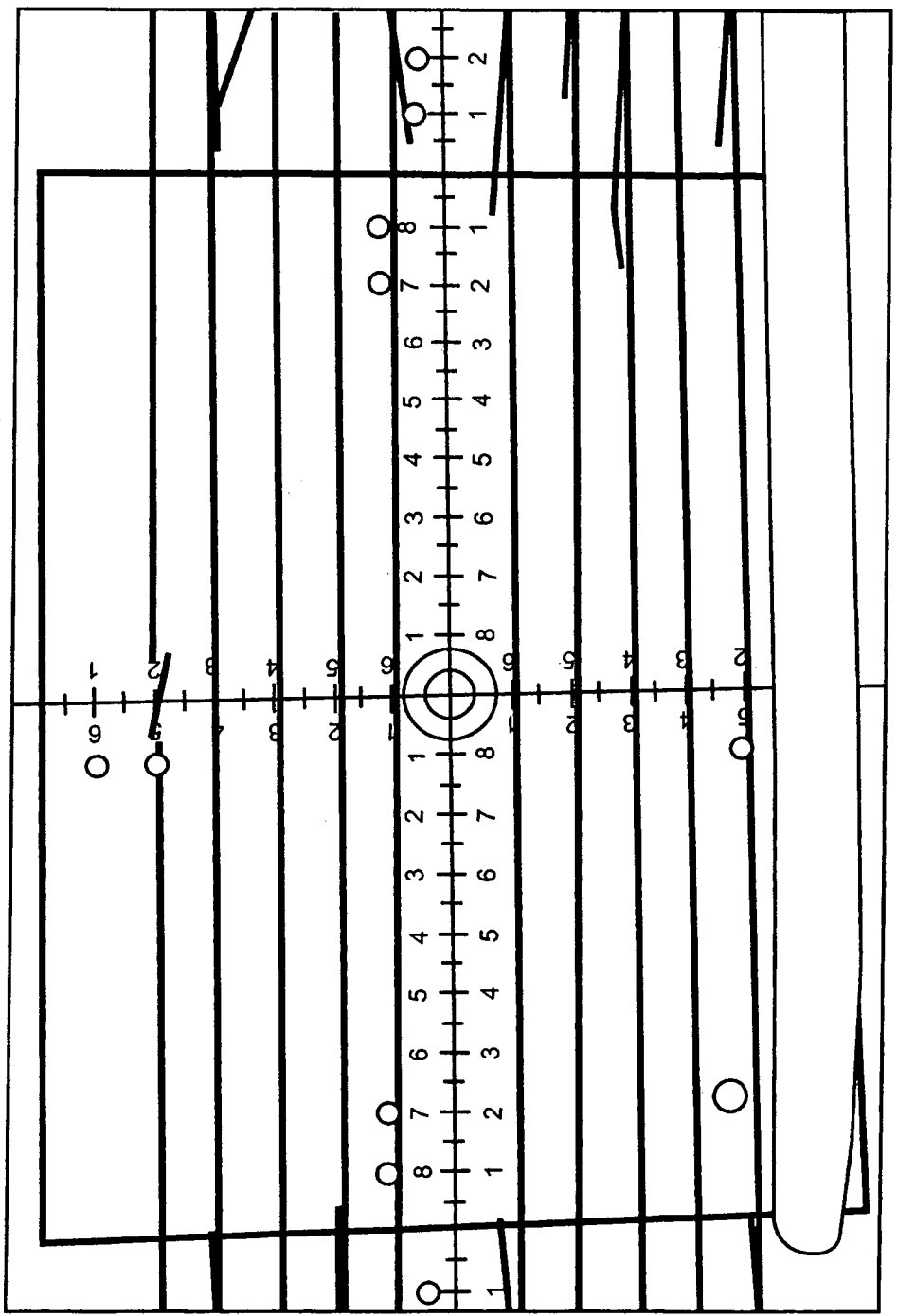
FIG. 11 is a view similar to FIG. 6, with the camera rotated 30° down and displaced 15° craniocaudally.

FIG. 6 shows a radiograph of a nail in alignment with a jig according to the invention where the camera is horizontal with respect to the jig. FIG. 7 shows the same arrangement before the jig has been moved into alignment with the nail. FIGS. 8-11 show views of the aligned assembly taken from different camera angles, and confirm that whichever view is selected, the alignment between the nail and the jig is within acceptable tolerances.

Figure 12:
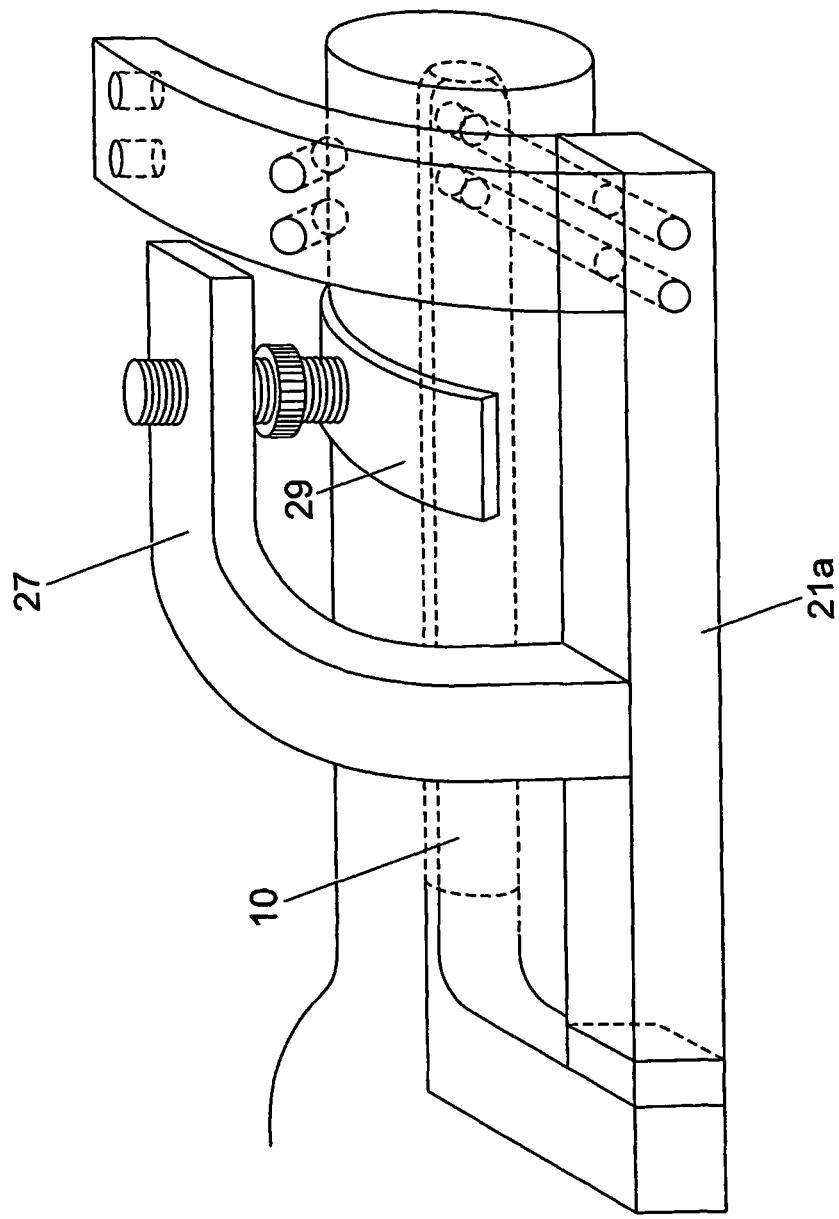
FIG. 12 is a view similar to FIG. 2 showing a further jig with an extension.

Modifications and improvements can be incorporated without departing from the scope of the invention. For example, in a complex version of the invention the arm can have (or can comprise) an extension to cover other faces of the limb; the extension can be in the form of an L-shaped or arcuate member being semi-cylindrical in form and typically describing 90°-180° of a circle. One exemplary view of an extension can be seen in FIG. 12, which permits holes to be drilled at various angles relative to one another, and is particularly useful for nails that have dorso-ventral and medio-lateral (or other intermediate) fixing holes at the distal ends. The arm in the FIG. 12 embodiment can be biased downwards and inwards relative to the limb, so that it needs to be moved in more than one plane to align the holes on the extension with the holes on the nail.

This can be achieved by providing more than one stabiliser arm; for example a second stabiliser arm that pushes the distal ends of the arm and the limb away from one another; or by locating the stabiliser arm at an intermediate position between the horizontal and vertical positions.

The wires/strips in the jigs need not be made from metal; any suitable radio-opaque material could be used instead.

Figure 13:
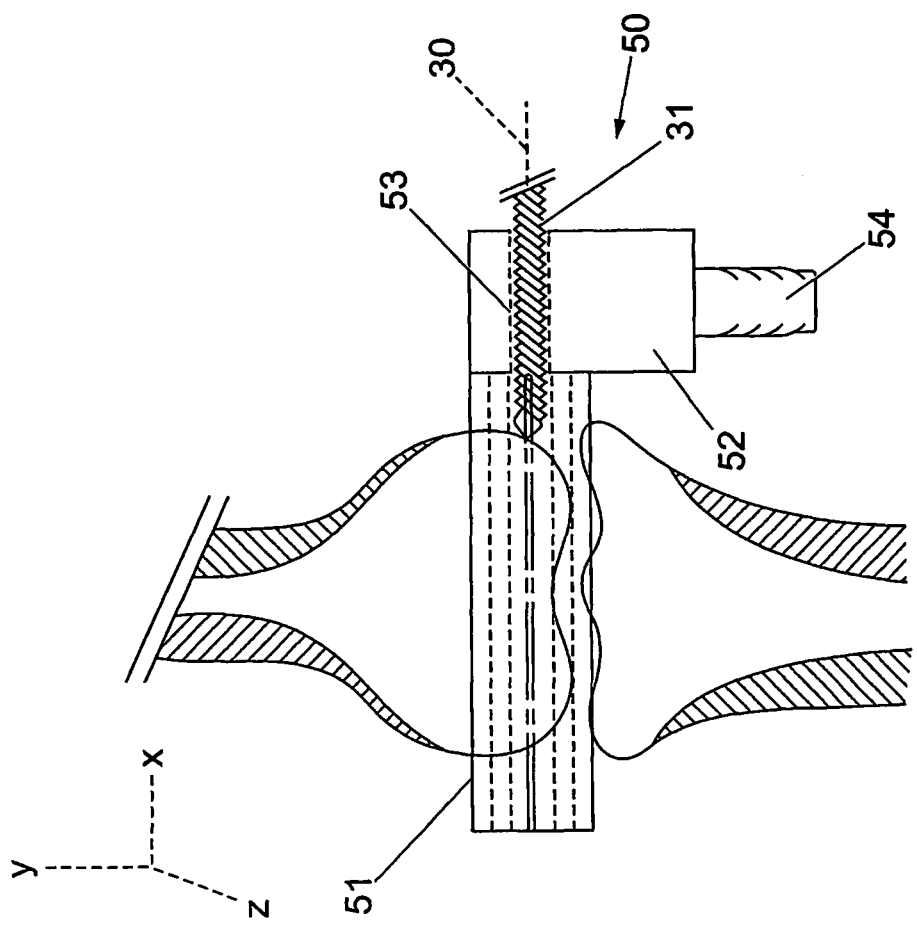
FIGS. 13, 14 and 15 show a further embodiment of apparatus for use with a guide wire, unattached to the patient's skeleton.
Figure 14:
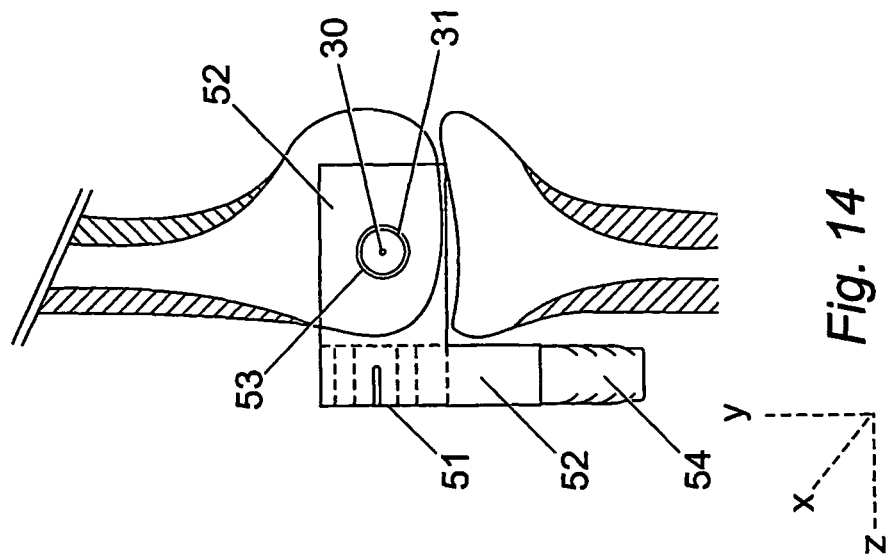
Figure 15:
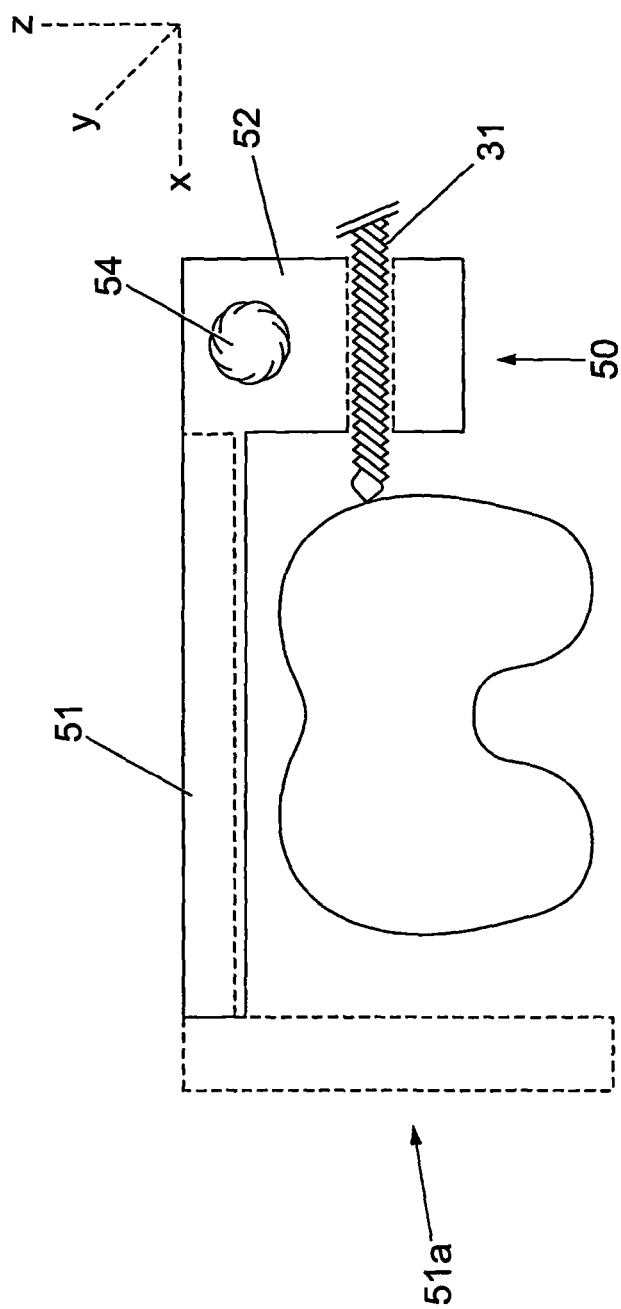

Certain embodiments of the invention do not need to have the jig physically attached to either the nail or the skeleton of the patient. For example, the jig could be hand held or could be adapted to firmly attach to the outside of the patient's limb and an image intensifier used to check that the jig is correctly aligned with the patient's bone. One such embodiment is shown in FIGS. 13-15. FIG. 13 shows an artero-posterior view of a knee joint into which a pin (not shown) is to be driven. FIGS. 14 and 15 show lateral and plan views of the joint respectively. The pin will be inserted through a hole drilled by a cannulated drill over a K-wire 30. The K-wire 30 is attached to a jig So having an arm 51, an L-shaped head 52 arranged perpendicular to the arm 51, a clamp 53 for a drill guide 31 or a K-wire 30, and a handle 54. The drill guide/K-wire clamp and the arm 51 are parallel to the X-axis shown in FIGS. 13 and 14. The arm 51 is formed of radio-translucent carbon fibre and incorporates at least one radio-opaque metal wire or strip etc as previously described. The arm 51 is rigidly attached to the K-wire.

In use, the handle 54 is manipulated so that the wire 30 is inserted into the bone to be pinned. The angle of insertion of the wire 30 is judged by observing the superimposed image of the strips in the arm 51 against the x-ray image of the bone. The angle of insertion can be chosen to place the K-wire 30 or to drill the hole in the most dense parts of the bone. If the wire 30 is going to pass through the upper surface of the bone, the jig 50 can be rotated around the Z-axis, to correct the path of the wire 30. Likewise, if the path will extend through the side of the bone, the jig can be rotated around the Y-axis to correct the path.

The jig 50 shown in FIGS. 13-15 can be used as a hand held guide without any requirement to attach the jig 50 to any part of the patient's body, to facilitate the accurate placement of guide wires, drills, screws and other fixings, with reference to anatomical landmarks, and not necessarily with reference to other implants in the body, such as bone nails or other implants. The jig can help the surgeon to identify the proposed path of insertion of the components or implants to be inserted.

The arm 51 in this embodiment can also extend around the joint to be viewed, as shown in the dotted lines on FIG. 15, which indicates an optional arm extension portion 51a of carbon fibre that incorporates wires or strips as previously indicated. The extension portion 51a is rigidly attached to the arm 51 at 90°, and allows a further view to superimpose the markers on the extension portion 51a on the lateral view of the joint, and enable further adjustment. This modified embodiment is especially useful for situations where the position of the components need to be checked in more than one plane, e.g. hip fractures, spinal surgery, internal organs that have been radiologically enhanced with contrast agents.

In some embodiments, the arm may be axially extendible, e.g. by having a telescopically extending portion that can be selectively extended and retracted to adjust the length of arm. One or both of the nail 10 and the arm may also have additional holes 12, so that the extension of the arm can be altered to align a selected pair or set of holes 12 and 22.

Figure 16:
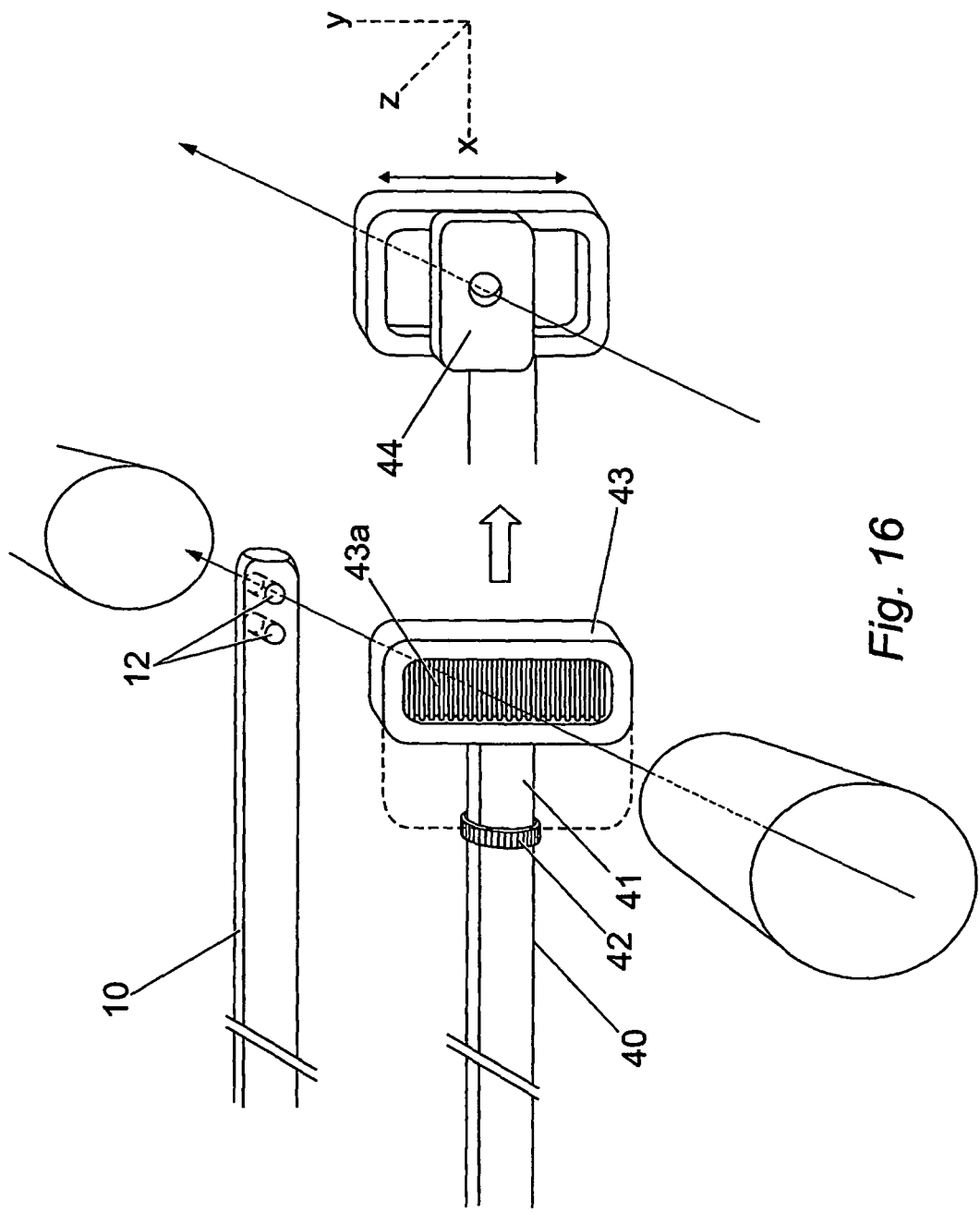
FIG. 16 shows a portion of a further embodiment of a jig with the capability of axial extension of a bar.

FIG. 16 shows an additional embodiment similar to the second, but where the arm comprises first and second pieces 40, 41 that slide telescopically relative to one another along the X-axis of the arm. The arm terminates in a head 43 that has a radio-translucent window insert 43a of carbon fibre or Perspex™ upon which is inscribed a radio-opaque leaded pattern of bars on each face of the window. In addition to being able to move axially along the X-axis of the arm, the head 43 can rotate around the X-axis. The patterns of bars on each face of the window insert 43a are offset with respect to one another and arranged to permit transmission of x-rays or light through the window only when the rotational position of the window around the X-axis is not precisely perpendicular to the nail 10. When the head 43 is precisely perpendicular to the nail, the offset patterns on the opposing faces of the window 43 overlap and occlude the window, preventing the transmission of x-rays or light, thereby confirming the correct rotational orientation of the window with respect to axis of the holes 12 in the nail.

Since the arm 40 has the same resilient hinge arrangement at it's proximal end, the arm can thus be adjusted around the Z-axis. Certain modified embodiments similar to FIG. 12 can also be produced with telescopic devices and can therefore be adjustable in three planes, including around the Y-axis.

When the head 43 has been moved to the correct axial position so that an optional radio-opaque marker in the centre of the window is axially aligned with the desired hole in the nail, the rotational alignment of the head 43 is adjusted by the above method to ensure that the head is in the correct rotational alignment with the axis of the hole 12 in the nail. At that point the window insert 43a can be removed from the head 43, and a variable height drill guide 44 can be inserted into the head 43 in its place. The drill guide 44 can be adjusted to align the hole on the guide with the hole on the nail and then locked in place on the head 43, before the hole is drilled.

When the first hole is drilled, e.g. for the distal hole 12 on the nail 10, the lockable ratchet on the arm can be unlocked and the head 43 can be moved from the position shown in FIG. 16 to the position shown in dotted lines where the hole on the guide 44 is in axial alignment with the proximal hole 12 on the nail 10. The rotational alignment can be checked again if desired, and the proximal hole can be drilled.

Figure 17:
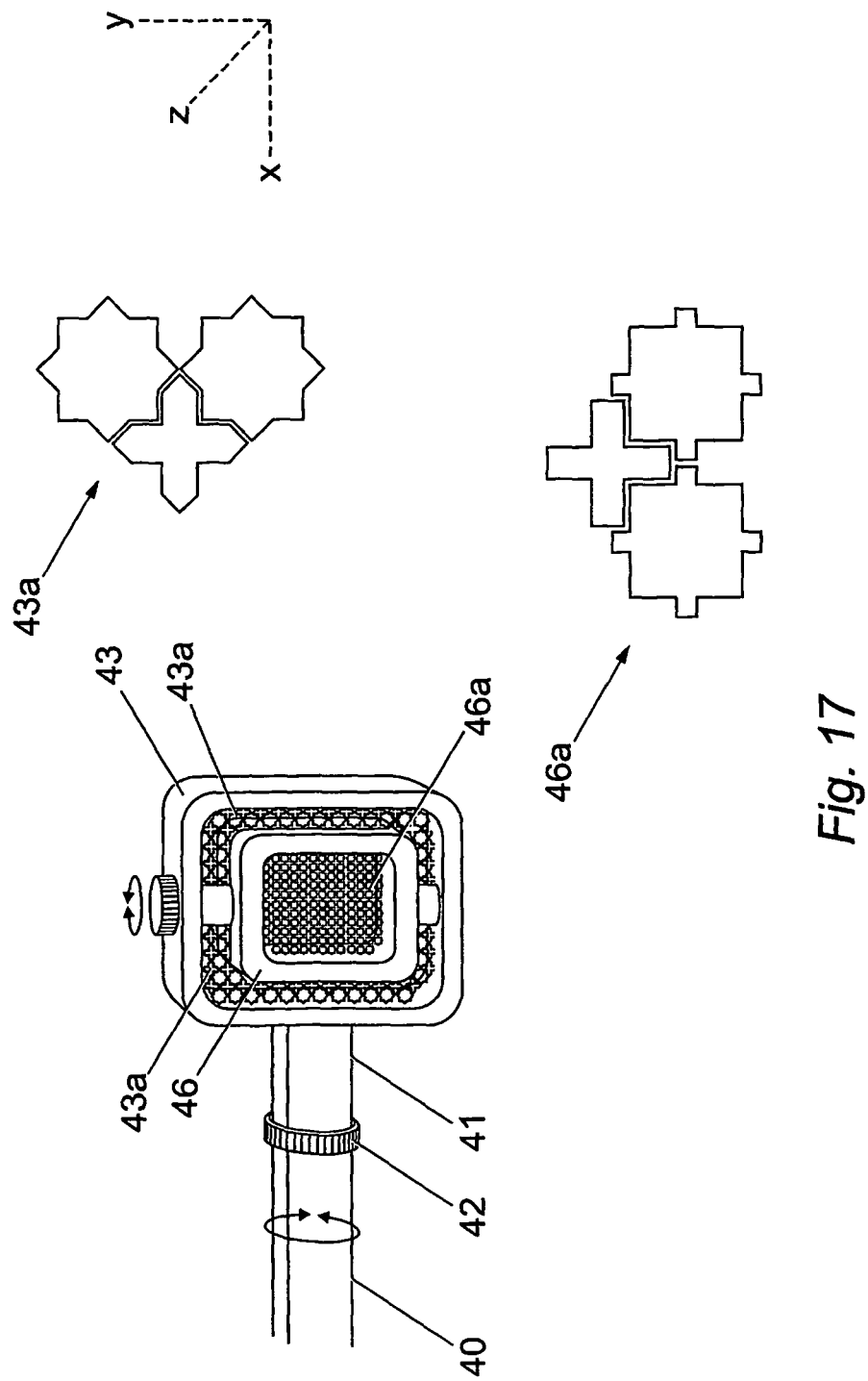
FIG. 17 shows a portion of a further embodiment of a jig with the capability of rotational movement of the distal end in more than one plane.

In the FIG. 17 embodiment, a further modification is shown in which the head 43 is axially extendible and rotationally adjustable around the X-axis as before. The head 43 has a window insert 43a but in this embodiment an additional window insert 46a is mounted on an optional gimballed frame 46 that is rotationally adjustable around the Y-axis.

The patterns of radio-opaque markings applied to the different sides of the windows can be various designs, with the proviso that the two patterns should in this embodiment complement one another to occlude the radiation only when the angle of light striking each window is precisely perpendicular to the plane of the window. Different patterns for each of the windows 43a, 46a are shown in FIG. 17.

The head 43 can be axially moved to a starting position where the axial alignment is verified with the windows out of rotational alignment with the nail so that the radiation can pass through both windows. In this position, the axial positioning in verified by lining up the central marker of the window 43a with the axis of the hole in the nail. The head 43 can be rotated around the X-axis to improve the view of the nail 10. When the desired axial alignment is achieved, the ratchet 42 is locked, and the head 43 is rotated around the X-axis until the image of the hole 12 in the nail 10 is occluded through the pattern on the window 43a, indicating that the correct alignment has been achieved around the X-axis. The rotational position of the head around the X-axis is optionally locked at this point, and the window insert 43a is optionally removed. The gimballed frame 46 is then rotated around the y axis, until the image of the hole 12 in the nail 10 through the pattern of the window 46a is occluded, indicating that the correct alignment around the Y-axis has been achieved. In this embodiment the rotational alignment of the head 43 around the X-axis is checked with a first window insert, and the rotational alignment of the gimballed frame 46 around the Y-axis is then checked using a different insert, but in certain embodiments the rotational alignment around the 2 axes can be checked by using the same window insert.

When the correct axial and rotational alignment has been achieved, the head can be locked in position, the window removed and the drill guide 44 inserted in place, for drilling the hole through the bone.

These embodiments can share all of the features of the other embodiments

Although the use of an image intensifier is described above, any x-ray emitter and detection device could alternatively be used to check the alignment of the nail and the jig.

Although the apparatus described here has two holes 12 and two further holes 22, different holes could be provided as required.

It should be noted that not all embodiments of the invention need to be used in conjunction with an intra-medullary nail. For example, the apparatus could also be a jig used to correctly align a fracture-securing pin, such as a hip pin. The jig would typically be secured to the patient's bone or to the exterior of the body. Viewing the jig and bone through an image intensifier, the position of the jig could then be adjusted to align radio-opaque markings of the jig with the bone or a particular feature on the bone. A guide wire could then be inserted through a hole in the jig, and a drill used to drill a hole in the bone for insertion of the pin. As in the embodiments described above, the use of the guide wire is optional and the pin and/or drill may be cannulated to fit over the guide wire.

The invention claimed is:

1. An assembly comprising:
    a jig for handling of at least one implant for insertion into a patient's body; and
    a support device for insertion into the patient's body, the support device having a longitudinal axis;
    wherein the jig has a proximal end adapted to connect to a proximal end of the support device and a distal end that is moveable with respect to the support device;
    wherein the distal end of the jig has a radio-translucent portion and a plurality of parallel, radio-opaque markings;
    wherein, in use, the distal end of the jig is constrained to move relative to the support device between a non-aligned position in which the radio-opaque markings are out of alignment with the axis of the support device, and an aligned position, in which the radio-opaque markings of the jig are aligned with the longitudinal axis of the support device.

2. An assembly as claimed in claim 1, wherein the jig has at least one rigid portion.

3. An assembly as claimed in claim 1, wherein the radio-opaque markings comprise at least one elongate element applied to the jig, the elongate element being selected from the group consisting of a strip and a line.

4. An assembly as claimed in claim 1, wherein the radio-opaque markings indicate the position to drill a respective hole to receive the at least one implant.

5. An assembly as claimed in claim 1, wherein the jig is adapted to receive at least one of the group consisting of a drill, a drill sleeve and a guide wire.

6. An assembly as claimed in claim 1, affixable to the body of the patient.

7. An assembly as claimed in claim 6, wherein the jig is adapted to be attached to the body at one end of the jig, and wherein the other end of the jig is inclined towards the body.

8. An assembly as claimed in claim 6, wherein the distal end of the jig is inclined out of the plane of the body.

9. An assembly as claimed in claim 6, wherein the jig is adapted to be attached to the body at only its proximal end; and wherein the adjustment mechanism is adapted to move the distal end of the jig into alignment with the body.

10. An assembly as claimed in claim 6, wherein the jig extends circumferentially around the body to allow lateral holes to be drilled through the body at different angles.

11. An assembly as claimed in claim 6, wherein the jig has an alignment adjustment mechanism to adjust the alignment of the apparatus relative to the support device.

12. An assembly as claimed in claim 11, wherein the alignment adjustment mechanism comprises a screw-threaded device that can adjust the alignment of the jig.

13. An assembly as claimed in claim 11, wherein the jig is resiliently biased out of alignment with the support device in the non-aligned position.

14. An assembly as claimed in claim 11, wherein the distal end of the jig is inclined towards the support device in the non-aligned position.

15. An assembly as claimed in claim 11, wherein one end of the jig is inclined out of the plane of the support device in the non-aligned position.

16. An assembly as claimed in claim 11, wherein the jig is adapted to be attached to the support device at only one end, and wherein the adjustment mechanism is adapted to move the other end of the jig into alignment with the support device.

17. An assembly as claimed in claim 1, wherein the support device comprises an intra-medullary nail to be placed in the medullary canal of the bone of a limb of a patient.

18. An assembly as claimed in claim 17, wherein the jig has an alignment adjustment mechanism to adjust the alignment of the jig relative to the nail.

19. An assembly as claimed in claim 18, wherein the alignment adjustment mechanism comprises a screw-threaded device that can adjust the alignment of the jig.

20. An assembly as claimed in claim 17, wherein the jig is resiliently biased out of alignment with the nail.

21. An assembly as claimed in claim 17, wherein the jig comprises a generally planar member that extends in a single plane that is parallel to the support device.

22. An assembly as claimed in claim 1, wherein the jig has an arm and a hinge to allow movement of the arm.

23. An assembly as claimed in claim 22, wherein the hinge is a resilient joint.

24. An assembly as claimed in claim 22, wherein the arm is formed in more than one plane.

25. An assembly as claimed in claim 22, wherein the arm is L-shaped.

26. An assembly as claimed in claim 22, wherein the arm is extendible.

27. An assembly as claimed in claim 22, wherein the arm is arcuate.

28. An assembly as claimed in claim 1, wherein the implant to be handled is a fixing for an intra-medullary nail.

29. An assembly as claimed in claim 28, wherein the implant is selected from the group consisting of antero-posterior, medio-lateral and diagonal fixings.

30. An assembly as claimed in claim 1, wherein the plurality of parallel, radio-opaque markings are selected from the group consisting of strips and lines.

31. An assembly as claimed in claim 1, wherein the jig includes an arm and a head, wherein the head has a radio-translucent window having first and second faces, each face being provided with a respective radio-opaque marking, the window being pivotable relative to the arm about an axis, whereby on illumination of the window with x-ray radiation, the extent of any overlap between the radio-opaque markings of the first and second faces indicates the orientation of the arm relative to the x-ray radiation.

32. An assembly as claimed in claim 31, wherein the markings of the first and second faces are offset from each other such that transmission of radiation is prevented when the plane of the window is perpendicular to the x-ray radiation.

33. An assembly as claimed in claim 31, wherein the, markings comprise bars.

34. An assembly as claimed in claim 31, wherein the first face has markings which are complementary to the markings of the second face.

35. An assembly as claimed in claim 31, wherein the window is pivotable about two perpendicular axes.

36. An assembly as claimed in claim 31, wherein first and second windows are provided, the first window being pivotable about a first axis and the second window being mounted on the first window and being pivotable relative thereto about a second axis that is perpendicular to the first axis.

37. An assembly as claimed in claim 1, further including a guide aperture to guide the path of the implant, wherein at least one of the radio-opaque markings is visible on insertion of the implant through the guide aperture.

38. A jig for handling of at least one implant for insertion into a patient's body, the jig having a proximal end adapted to connect to a support device and a distal end that is moveable with respect to the proximal end;
   wherein the distal end of the jig has a radio-translucent window and wherein different two patterns of radio-opaque markings are applied to opposite faces of the radio-translucent window; and
   wherein the two patterns of radio-opaque markings combine to occlude radiation passing through the window only when the angle of the radiation striking each face is perpendicular to the plane of the window.

39. A jig as claimed in claim 38, wherein the window is pivotable.

40. A jig as claimed in claim 39, wherein the window is pivotable about two perpendicular axes.

41. A jig as claimed in claim 30, wherein first and second windows are provided, the first window being pivotable about a first axis and the second window being mounted on the first window and being pivotable relative thereto about a second axis that is perpendicular to the first axis.

42. A jig as claimed in claim 38, wherein the window is removably located in a head portion of the jig, the head portion of the jig also being adapted to support a drill guide after removal of the window.

* * * * *